United States Patent [19]

Rossini et al.

[11] Patent Number: 5,260,497
[45] Date of Patent: Nov. 9, 1993

[54] CATALYTIC SYSTEM FOR CONVERTING METHANE INTO HIGHER HYDROCARBONS

[75] Inventors: Stefano Rossini, Milan; Orfeo Forlani, San Donato Milanese; Domenico Sanfilippo, Paullo, all of Italy

[73] Assignee: Snamprogetti S.p.A., Milan, Italy

[21] Appl. No.: 876,140

[22] Filed: Apr. 29, 1992

Related U.S. Application Data

[63] Continuation of Ser. No. 650,968, Feb. 5, 1991, abandoned.

[30] Foreign Application Priority Data

Feb. 7, 1990 [IT]  Italy ................ 19284 A/90

[51] Int. Cl.$^5$ .................. B01J 21/06; B01J 21/08; B01J 23/02; B01J 23/04
[52] U.S. Cl. ............... 502/243; 502/303; 502/344; 502/250; 502/341
[58] Field of Search ........... 502/303, 344, 243, 250, 502/341

[56] References Cited

U.S. PATENT DOCUMENTS

| | | | |
|---|---|---|---|
| 3,926,854 | 12/1975 | Whelan et al. | 502/303 |
| 4,656,155 | 4/1987 | Josefowicz | 502/344 X |
| 4,826,796 | 5/1989 | Erekson et al. | 502/341 X |
| 4,971,940 | 11/1990 | Kaminsky et al. | 502/341 X |

FOREIGN PATENT DOCUMENTS 0177327 4/1986 European Pat. Off. .
WO86/07351 12/1986 PCT Int'l Appl. .

*Primary Examiner*—W. J. Shine
*Assistant Examiner*—Douglas T. McGinty
*Attorney, Agent, or Firm*—Oblon, Spivak, McClelland, Maier & Neustadt

[57] ABSTRACT

A catalytic system for converting methane into higher hydrocarbons, which catalytic system falls within the scope of the following empirical formula:

$$A_a\ B_b\ C_c\ O_x$$

in which:

A is an element selected from the group consisting of Si, Ti, Zr;
B is an element selected from the group consisting of La, Sc, Y, and
C is an alkali or alkali-earth metal, wherein
a is a numeral comprised within the range of from 0.01 to 10,
b is a numeral comprised within the range of from 0.01 to 10,
c is a numeral comprised within the range of from 0.01 to 10,
X is a numeral which satisfies the valency state with which the several elements appear in the catalytic system, is disclosed.

1 Claim, No Drawings

CATALYTIC SYSTEM FOR CONVERTING METHANE INTO HIGHER HYDROCARBONS

This application is a continuation of application Ser. No. 07/650,968, filed on Feb. 5, 1991, now abandoned.

The present invention relates to a heterogeneous catalytic system capable of converting methane into higher hydrocarbons, mainly $C_2$ hydrocarbons.

The largest methane source is natural gas, an energy reserve of paramount importance, whose role seems to be destined to increase in future, as a source for chemicals.

In fact, to date, approximately 90% of natural gas is used as fuel, with the residual 10% being used in the indirect production of methanol, ammonia and derivatives thereof, chlorine-containing compounds and other minor compounds. The composition of natural gas varies according to the source it comes from, but methane is undoubtedly the major component thereof, in that it may even comprise up to 99% by volume, the remainder being light hydrocarbons, inert gases and chemical species with acidic character ($CO_2$, $H_2S$).

Therefore, fully exploiting this source of carbon atoms is of uppermost importance.

The poor reactivity for functionalization shown by light hydrocarbons and in particular methane has always constituted a limit to this exploitation, so that at present methane is being mainly used as a fuel. In spite of that, the problem of transport has to be coped with, because methane reservoirs are generally located in regions far away from the areas where methane is used. The transport technologies known from the present state of the art are practicable with considerable financial costs. They can be summarized as: transport via pipeline and via gas liquefaction/re-vapourization.

The possibility of converting methane into easier handled compounds is hence extremely important.

Furthermore, the possibility of directly obtaining olefins from methane, such as ethylene and propylene, may open a considerable chemical industry based on methane, or natural gas.

Methane conversion can be accomplished according to several routes involving the use of co-reactants and/or catalysts, or not.

Simple pyrolysis or dehydrogenation into $C_2$ hydrocarbons requires high temperatures (higher than 1000° C.) and extremely short contact times, owing to thermodynamic constraints. Patent literature reports some examples of catalytic systems capable of addressing the reaction: see, e.g., U.S. Pat. Nos. 1,656,813; 1,687,890; 1,851,726; 1,863,212; 1,922,918; 1,945,960; 1,958,648; 1,986,238. This route is not extremely selective and results to be scarcely used in practice.

The use of co-reactants can be accomplished in the presence of catalysts, or not.

As regards the first reaction version, the following were proposed: oxygen to yield methanol and formaldehyde [Chem. Rew. 85(4), 235 (1985)], or chlorine (Benson process, U.S. Pat. No. 4,199,533), to obtain higher hydrocarbons. A recent Japanese patent application JP 88/222126 claims the synthesis of hydrocarbons, mainly $C_2$ hydrocarbons, by directly reacting methane and oxygen under pressure.

Methane conversion is mainly performed through catalytic processes, with co-reactants taking part to the reaction.

A first example dates back to the Forties: oxygen-containing products were obtained on a commercial scale using NO as the oxidant (Fiat Report No. 1085, Mar. 31, 1947).

The reaction to obtain methanol and formaldehyde is mainly catalysed by molybdenum-based compounds, variously modified [see GB 1,398,385 (1971) to Imperial Chemical Industries and GB 1,398,385 (1975) to British Gas Corporation]; a special system uses iron sulfate in an acidic solution (DE 3,101,024).

The formation of hydrocarbon mixtures prevailingly containing $C_2$ compounds is named "oxidative coupling" and is generally carried out in the presence of oxygen or air, with the catalysts being of prevailingly oxide character.

The two reactants can be fed either alternatively or simultaneously to the catalyst. In the first case, the active oxides are those of low-melting metals such as cadmium, indium, tin, antimony, thallium, lead, bismuth, manganese, and so forth, either as such or modified [J. Catal. 73, 9–19 (1982) Union Carbide; U.S. Pat. Nos. 4,443,644 to 7; U.S. Pat. Nos. 4,444,984; 4,495,374; 4,499,322 and 4,560,821 to Atlantic Richfield Co.].

In the second case, oxides of alkaline-earth metals modified with alkali metals are essentially used [U.S. Pat. Nos. 4,620,057 and 4,654,460 to Phillips Petroleum; U.S. Pat. Nos. 4,801,7632 to Atlantic Richfield Co.].

A peculiar catalysis is the catalysis performed by solid super-acids (G. A. Olah U.S. Pat. No. 4,513,164), in which, in the presence of oxidants always $C_2$ hydrocarbons are obtained.

From relevant technical literature, other systems are known, which are capable of converting methane into higher hydrocarbons: metals belonging to the first transition series, used in general in their oxides, variously modified with alkali metal oxides or halides; and rare earths are mentioned.

A variety of claimed materials compatibly exist, with different compositions; see:
FR 2,607,804 to Inst. Fr. Petrole: (LiBr/KBr);
U.S. Pat. No. 4,751,336 to Amoco Corp.: (1% by weight KBr/calsicat D);
JP 88/77826.

The above mentioned catalysts do not allow in general high values of conversion to methane to be coupled with high values of productivity and selectivity.

Furthermore, many of these catalysts undergo a fast ageing, consequently rapidly losing their activity and selectivity.

A particular catalytic composition was found now which is highly active and selective in the oxidative coupling of methane. Such catalytic composition makes it possible the drawbacks occurring when catalysts known from the prior art are used, to be reduced.

The catalytic system according to the present invention is characterized in that it falls within the scope of the following empyrical formula:

$$A_a\ B_b\ C_c\ O_x \qquad (I)$$

in which:
A is an element selected from the group consisting of Ge, Si, Sn, Ti, Zr
B is an element selected from the group consisting of La, Sc, Y
C is an alkali or alkali-earth metal a is a numeral comprised within the range of from 0.01 to 10 and preferably comprised within the range of from 0.25 to 2, b is a numeral comprised within the range of from 0.01 to 10, and preferably comprised within the range of from 0.05 to 2.5, c is a numeral comprised within the range of from 0.01 to 10, and preferably comprised within the range of from 0.05 to 2.5.

x is a numeral which satisfies the valency state with which the several elements appear in the catalytic system.

The preferred elements are titanium and zirconium for "A" component, yttrium and lanthanum for "B" component, alkali metals and, in particular, sodium for "C" component.

The catalytic system according to the present invention can be suitably prepared according to one of the methodologies known from literature for analogue compositions.

In particular, such methods can be:
slurry drying (dry mixing);
spray drying;
gelation;
precipitation;
co-precipitation;
impregnation.

The methodologies are preferably selected as a function of the different starting materials.

Sometimes, carrying out also a drying treatment may prove either necessary or advantageous.

The so obtained material, said the "catalyst precursor", is calcined at a high temperature (not higher than 1000° C.) in several ways.

The thermal cycle used by us to prepare the catalysts specified in the examples, is as follows:

| Cycle sequence (°C.) | Heating/Cooling rate (°C./h) | Time (h) |
| --- | --- | --- |
| Room temp. → 150 | 65.0 | 2.0 |
| 150 | — | 2.0 |
| 150 → 300 | 75.0 | 2.0 |
| 300 | — | 4.0 |
| 300 → 800 | 140.0 | 3.6 |
| 800 | — | 4.0 |
| 800 → Room temp. | 40.0 | 19.5 |

A further object of the present invention is the process for converting methane into higher hydrocarbons, mainly $C_2$ hydrocarbons.

Such a process is characterized in that a gas mixture containing methane and oxygen in a mutual volume ratio comprised within the range of from 0.1 to 100, and preferably comprised within the range of from 0.5 to 25, possibly diluted with inert gases, is brought into contact with the catalytic system represented by the above formula (1), by operating at a temperature comprised within the range of from 400° to 1000° C., and preferably comprised within the range of from 550° to 900° C., under a pressure comprised within the range of from 0.9 to 10 atm, preferably comprised within the range of from 0.99 to 2.5 atm, and at a space velocity (GHSV) comprised within the range of from 100 to 50,000 $h^{-1}$, preferably comprised within the range of from 500 to 4500 $h^{-1}$.

Some examples are now given to better illustrate the invention. In no way should such examples be regarded as being limitative of the same invention.

EXAMPLE 1

A catalyst Ti:La:Na=1:1:1 is prepared as follows. 28.90 g of $LaNO_3.6H_2O$ and 5.40 g of $NaNO_3$ are dissolved with heating in 150 ml of ethanol. Then 15.73 g (equivalent to about 15.04 ml) of $Ti(OEt)_4$ admixed with 30 ml of ethanol are added. The pseudo-gelation of the solution is caused by the addition of a small amount of $H_2O$. The whole mixture is oven-dried at 80° C. over 22 hours, and the precursor is subsequently calcined according to the above scheme.

EXAMPLE 2

The catalyst Ti:La:Na=1:2:1 is obtained by concentrating by evaporation an aqueous solution (250 ml) of 2.86 g of $TiO_2$, 25.81 g of $LaNO_3.6H_2O$ and 2.84 g of $NaNO_3$ until a rather thick liquid is obtained. The thick liquid is oven-dried at about 100° C. for 24 hours and the resulting solid is calcined according to the scheme reported hereinabove.

EXAMPLES 3-4

By operating in the same way as of Example 1, the following catalysts are prepared: Ti:La:Li=1:1:1 catalyst (Example 3) from 28.92 g of $LaNO_3.6H_2O$ and 4.60 g of $LiNO_3$ in 150 ml of ethanol, to which 15.44 g (equivalent to 13.80 ml) of $Ti(OEt)_4$ admixed with 30 ml of ethanol are added; and Ti:La:K=1:1:1 catalyst (Example 4) from 28.95 g of $LaNO_3.6H_2O$ and 6.75 g of $KNO_3$ in 150 ml of ethanol+30 ml of $H_2O$, to which 15.57 g (equivalent to 13.91 ml) of $Ti(OEt)_4$ admixed with 30 ml of ethanol are added.

EXAMPLES 5-6

According to the same modalities as described in Example 2, the catalysts Ti:La:Mg=1:1:1 (Example 5) and Ti:La:Ca=1:1:1 (Example 6) are prepared using the reactants described in Table 1.

TABLE 1

|  | Example 5 (g) | Example 6 (g) |
| --- | --- | --- |
| $TiO_2$ | 4.42 | 4.43 |
| $LaNO_3.6H_2O$ | 23.68 | 23.73 |
| $Mg(CH_3COO)_2.4H_2O$ | 12.18 | — |
| $Ca(NO_3)_2$ | — | 13.49 |
| $H_2O$ | 250 | 250 |

EXAMPLE 7

The catalyst Ti:Y:Na=1:1:1 is prepared in the same way as of Example 1, from 23.57 g of $Y(NO_3)_3.6H_2O$ and 4.90 g of $NaNO_3$, which are dissolved in 160 ml of ethanol, to which 13.44 g(=12.01 ml) of $Ti(OEt)_4$, admixed with 20 ml of ethanol, are added.

When the ethanolic solution of $Ti(OEt)_4$ is added, a nearly instantaneous pseudo-gelation takes place, so that the small amount of water of Example 1 is not added.

EXAMPLES 8-9

According to as disclosed for Example 2, the catalysts Zr:La:Na=1:1:1 (Example 8) and Zr:Y:Na=1:1:1 (Example 9) are prepared using the materials and amounts shown in Table 2.

TABLE 2

|  | Example 8 (g) | Example 9 (g) |
|---|---|---|
| $ZrO_2$ | 6.84 | 6.91 |
| $LaNO_3.6H_2O$ | 23.83 | — |
| $Y(NO_3)_3.6H_2O$ | — | 23.26 |
| $NaNO_3$ | 4.45 | 4.86 |
| $H_2O$ | 250 | 250 |

EXAMPLE 10

28.89 g of $LaNO_3.6H_2O$ and 5.68 g of $NaNO_3$ are dissolved in 16 ml of ethanol+7.5 ml of $H_2O$. By slightly heating the mixture, all such solids are almost completely dissolved. 14.85 g of $Si(OEt)_4$ is added, and a pseudo-gelation is obtained by slightly increasing the temperature. The reaction mixture is left stading in an oven at 75° C. over 20 hours, and the reaction mixture is calcined according to the above reported cycle.

EXAMPLES 11–51

The materials prepared as disclosed in Examples 1–10 were submitted to tests for their catalytic activity, according to the following modalities. Granulates of 20–40 mesh of size are charged to a quartz reactor (catalyst volume=2 ml) and are kept under a flowing nitrogen stream while the temperature is increased up to 300° C. The methane/air mixture is then fed. The flow rates normally used have the following values:
methane 22 (Nml/minute) and air at the necessary flow rate to obtain the desired value of $CH_4/O_2$ ratio (see Table 3).

TABLE 3

| Ratio of $CH_4/O_2$ | 2 | 5 | 10 | 20 |
|---|---|---|---|---|
| Air (Nml/minute) | 52.4 | 21.0 | 10.5 | 5.3 |

The results obtained are reported in Table 4.

TABLE 4

| Example | Catalyst of Example | T (°C.) | Ratio of $CH_4/O_2$ | $CH_4$ conversion (%) | Selectivity (%) | | | |
|---|---|---|---|---|---|---|---|---|
| | | | | | $CO_x$ | $C_2H_4$ | $C_2H_6$ | RH ($C_2+$) |
| 11 | 1 | 700 | 11.2 | 8.8 | 46.4 | 14.4 | 36.3 | 2.9 |
| 12 | 1 | 750 | 10.4 | 13.4 | 30.0 | 27.0 | 34.1 | 8.9 |
| 13 | 1 | 750 | 5.3 | 19.6 | 43.2 | 24.9 | 26.7 | 5.2 |
| 14 | 1 | 750 | 2.2 | 38.3 | 58.4 | 21.7 | 16.4 | 3.5 |
| 15 | 1 | 750 | 22.3 | 5.4 | 24.7 | 33.1 | 37.5 | 4.7 |
| 16 | 2 | 700 | 10.8 | 8.3 | 42.0 | 18.3 | 37.6 | 2.2 |
| 17 | 2 | 750 | 10.8 | 10.5 | 39.0 | 25.9 | 32.6 | 2.5 |
| 18 | 2 | 750 | 5.2 | 19.3 | 43.1 | 25.5 | 28.0 | 3.5 |
| 19 | 3 | 700 | 10.6 | 8.8 | 50.7 | 13.2 | 33.8 | 2.3 |
| 20 | 3 | 750 | 9.8 | 11.4 | 36.6 | 25.9 | 31.8 | 5.7 |
| 21 | 3 | 750 | 5.1 | 18.1 | 47.6 | 23.9 | 26.0 | 2.5 |
| 22 | 3 | 750 | 2.2 | 35.8 | 63.0 | 20.4 | 15.8 | 0.8 |
| 23 | 4 | 702 | 10.8 | 6.3 | 63.3 | 10.0 | 26.7 | 0.0 |
| 24 | 4 | 751 | 10.8 | 8.6 | 52.0 | 24.6 | 23.4 | 0.0 |
| 25 | 4 | 751 | 5.4 | 14.9 | 62.4 | 18.5 | 19.1 | 0.0 |
| 26 | 5 | 700 | 9.0 | 8.5 | 69.7 | 8.0 | 22.3 | 0.0 |
| 27 | 5 | 750 | 9.0 | 9.4 | 55.7 | 16.1 | 24.7 | 3.5 |
| 28 | 6 | 650 | 8.8 | 8.6 | 62.0 | 5.9 | 29.2 | 2.9 |
| 29 | 6 | 700 | 8.8 | 9.5 | 52.2 | 12.7 | 32.7 | 2.4 |
| 30 | 6 | 750 | 8.8 | 11.6 | 48.4 | 20.5 | 28.4 | 2.7 |
| 31 | 6 | 750 | 23.0 | 4.6 | 30.0 | 26.8 | 42.0 | 1.2 |
| 32 | 6 | 750 | 4.9 | 17.4 | 49.1 | 23.0 | 24.6 | 3.2 |
| 33 | 6 | 750 | 2.1 | 34.7 | 65.4 | 18.3 | 14.6 | 1.7 |
| 34 | 7 | 700 | 10.0 | 8.2 | 55.6 | 13.7 | 29.6 | 1.1 |
| 35 | 7 | 750 | 10.1 | 9.5 | 42.6 | 22.9 | 31.4 | 3.1 |
| 36 | 7 | 750 | 5.1 | 17.0 | 51.4 | 21.8 | 24.3 | 2.5 |
| 37 | 7 | 750 | 2.1 | 34.8 | 64.0 | 17.0 | 15.7 | 3.3 |
| 38 | 8 | 702 | 10.6 | 8.6 | 37.7 | 20.3 | 36.9 | 5.1 |
| 39 | 8 | 754 | 10.6 | 13.1 | 40.4 | 26.8 | 28.7 | 4.1 |
| 40 | 8 | 753 | 5.1 | 19.5 | 39.3 | 30.0 | 24.5 | 6.3 |
| 41 | 8 | 753 | 2.1 | 38.3 | 56.1 | 24.3 | 15.6 | 4.0 |
| 42 | 9 | 702 | 9.5 | 10.4 | 41.4 | 21.4 | 33.9 | 3.3 |
| 43 | 9 | 760 | 9.6 | 11.3 | 35.4 | 28.5 | 31.9 | 4.2 |
| 44 | 9 | 754 | 5.0 | 19.4 | 43.0 | 25.1 | 24.5 | 7.4 |
| 45 | 9 | 751 | 2.1 | 37.5 | 57.7 | 20.1 | 15.9 | 6.3 |
| 46 | 9 | 751 | 23.9 | 5.5 | 26.7 | 28.7 | 42.3 | 2.3 |
| 47 | 10 | 695 | 8.7 | 10.6 | 49.9 | 17.7 | 30.6 | 1.8 |
| 48 | 10 | 748 | 8.8 | 12.4 | 38.6 | 28.9 | 28.2 | 4.3 |
| 49 | 10 | 750 | 4.7 | 20.3 | 46.9 | 25.3 | 22.3 | 5.5 |
| 50 | 10 | 750 | 15.8 | 8.0 | 33.5 | 29.6 | 31.9 | 5.0 |
| 51 | 10 | 750 | 1.8 | 39.2 | 64.9 | 19.5 | 14.1 | 1.5 |

We claim:

1. Catalytic system for converting methane into higher hydrocarbons, consisting essentially of a heterogeneous mixture having the following empirical formula:

$$A_a \, B_b \, C_c \, O_x \qquad (I)$$

wherein:
A is an element selected from the group consisting of Si, Ti and Zr;
B is an element selected from the group consisting of La, Sc and Y;
C is an alkali or alkaline-earth metal;
a is a numeral comprised within the range of from 0.25 to 2;
b is a numeral comprised within the range of from 0.05 to 2.5;
c is a numeral comprised within the range of from 0.05 to 2.5;
x is a numeral which satisfies the valency state with which the several elements appear in the catalytic system;
and when C is an alkali metal the ratio a:b is from 0.5 to 10 and the ratio c:b is from 0.5 to 50.

* * * * *